United States Patent [19]

Gengler

[11] Patent Number: 4,587,955
[45] Date of Patent: May 13, 1986

[54] LATCH FOR SECURING AN ARTIFICIAL SPHINCTER

[75] Inventor: Jeffrey R. Gengler, Milwaukee, Wis.

[73] Assignee: Medical Engineering Corporation, Racine, Wis.

[21] Appl. No.: 663,287

[22] Filed: Oct. 22, 1984

[51] Int. Cl.[4] .......................... A61B 19/00; A61F 1/00
[52] U.S. Cl. ............................ 128/1 R; 128/DIG. 25; 24/644; 24/702; 24/580; 24/16 PB; 623/14
[58] Field of Search .................... 128/DIG. 25, 1 R; 24/702, 16 PB, 644, 580, 589; 3/1

[56] References Cited

U.S. PATENT DOCUMENTS

| | | | |
|---|---|---|---|
| 2,956,324 | 10/1960 | Kline | 24/702 |
| 3,979,801 | 9/1976 | Tareau | 24/580 |
| 4,161,806 | 7/1979 | Hennisse et al. | 24/580 |
| 4,408,597 | 11/1983 | Tenney, Jr. | 128/1 R |
| 4,509,710 | 4/1985 | Cooper et al. | 24/16 PB |

FOREIGN PATENT DOCUMENTS 1423840  11/1964  Switzerland ................. 24/644

Primary Examiner—Richard J. Apley
Assistant Examiner—David J. Isabella
Attorney, Agent, or Firm—Stuart E. Krieger; Richard H. Brink; Isaac Jarkovsky

[57] ABSTRACT

A latch for securing the ends of a belt together so as to encircle an inflatable cuff of an artificial sphincter. The latch includes two rotatable components with cavities which receive the belt ends when the components are suitably rotated and capture the belt ends within the latch when the belt is in tension.

8 Claims, 5 Drawing Figures

LATCH FOR SECURING AN ARTIFICIAL SPHINCTER

BACKGROUND OF THE INVENTION

1. Field of the Invention

The present invention relates generally to devices for controlling incontinence and more particularly to a mechanical latch for securing an artificial sphincter device within the body.

2. Description of the Prior Art

Natural sphincters enable people to control the discharge of body wastes. Many people, however, lose continence or the ability to control voiding functions of the urinary tract or colon because of malfunctions of the sphincter through trauma, birth defect, disease or surgical intervention. One way to help such people retain control of the voiding function is with an artificial sphincter which occludes the affected organ or vessel.

Several artificial sphincter devices have been developed, see e.g. U.S. Pat. No. 4,167,952 to Reinicke, which allow patients to regain control of the colon or urinary tract. These devices typically include a tourniquet or cuff section which can be pressurized to occlude the selected vessel, for example, the colon or urethra. The tourniquet or cuff must be secured about the vessel in order to function. This was previously accomplished with sutures; however, this technique is time consuming and subjects the sphincter to possible damage by the suture needle. In addition, securing the cuff in this manner can interfere with the blood supply to the vessel wall. When securing the cuff to the colon, care should be taken not to impede the blood vessels in the mesentery connecting the colon to the peritoneum.

Artificial sphincters have also been secured in place by mechanical latches. However, some of these latches may permit the tourniquet or cuff to disengage, thereby incapacitating the device and necessitating further surgery for the patient. While there are some mechanical latches for which disengagement is not a major problem, these devices typically employ elaborate securing techniques, some of which require the use of special tools.

It is the general object of the present invention to provide a latch for securing the belt encircling an artificial sphincter which can be quickly installed and is simple and reliable.

It is another object of the present invention to provide a mechanical latch which stays secure within the body, but can be easily removed when necessary.

SUMMARY

These and other objects are obtained by the mechanical latch of the present invention which secures a belt about an inflatable cuff portion of an artificial sphincter so as to maintain the cuff in operable position about a selected body vessel, e.g. the colon or urethra. The present invention is a latch which includes two components mounted on a common axle, pin or rod so that least one of the components is rotatable to some extent about the axle relative to the other component. Each component is equipped with at least one cavity capable of receiving a portion of the belt end. Each cavity is accessible for receipt or removal of the belt portion upon suitable rotation of one of the components relative to the other. When the cuff is positioned about the vessel and the belt ends are secured to the latch, the belt is in tension and the components align into a stabilized position with the cavities being inaccessible. This orientation prevents release of the inserted belt end.

The artificial sphincter includes a belt for encircling the cuff positioned around the circumference of the vessel. This belt preferably has a pair of ends, with at least one of the ends being bifurcated into two spaced apart flexible fingers, each finger terminating in an enlarged bead. The preferred latch for this type of belt includes two components which are independently rotatable about the pin. Each component includes a surface opposing an adjacent surface in the other component, and two cavities which are predeterminedly dimensioned for snugly accommodating a bead inserted from each of the opposing belt ends. Each cavity has a port in the corresponding opposing surface. A slit extends from each cavity through the corresponding component to the exterior. The slit permits the finger portion to extend therethrough when the bead is inserted into the cavity. Upon suitable rotation of at least one of the components, each of the ports is externally accessible, and insertion or removal of the bead is possible. The ports are inaccessible when the components are in the stabilized position and release of the inserted beads and corresponding belt end is prevented.

BRIEF DESCRIPTION OF THE DRAWINGS

The foregoing and other objects, characteristics and advantages will be more clearly understood from the following detailed description when read in conjunction with the accompanying drawings, in which.

DETAILED DESCRIPTION OF PREFERRED EMBODIMENT

Figure 1:
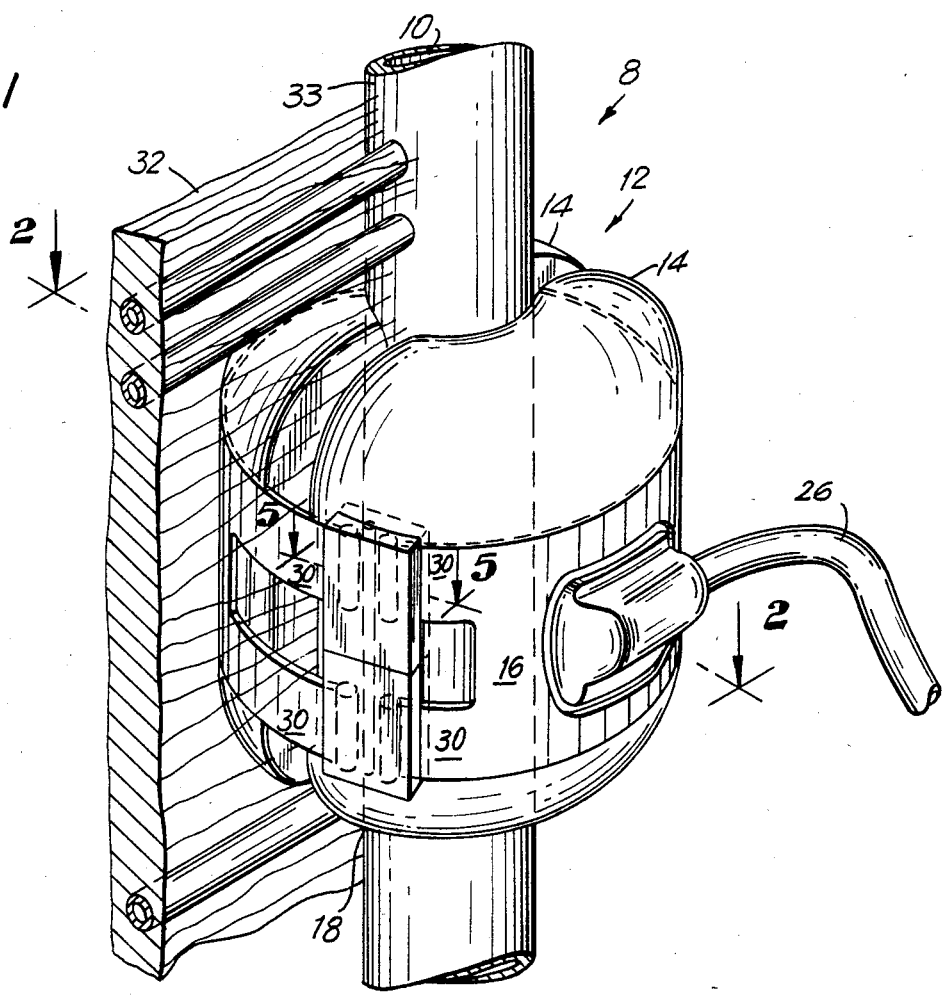
FIG. 1 is a perspective view of an artificial sphincter device.
Figure 2:
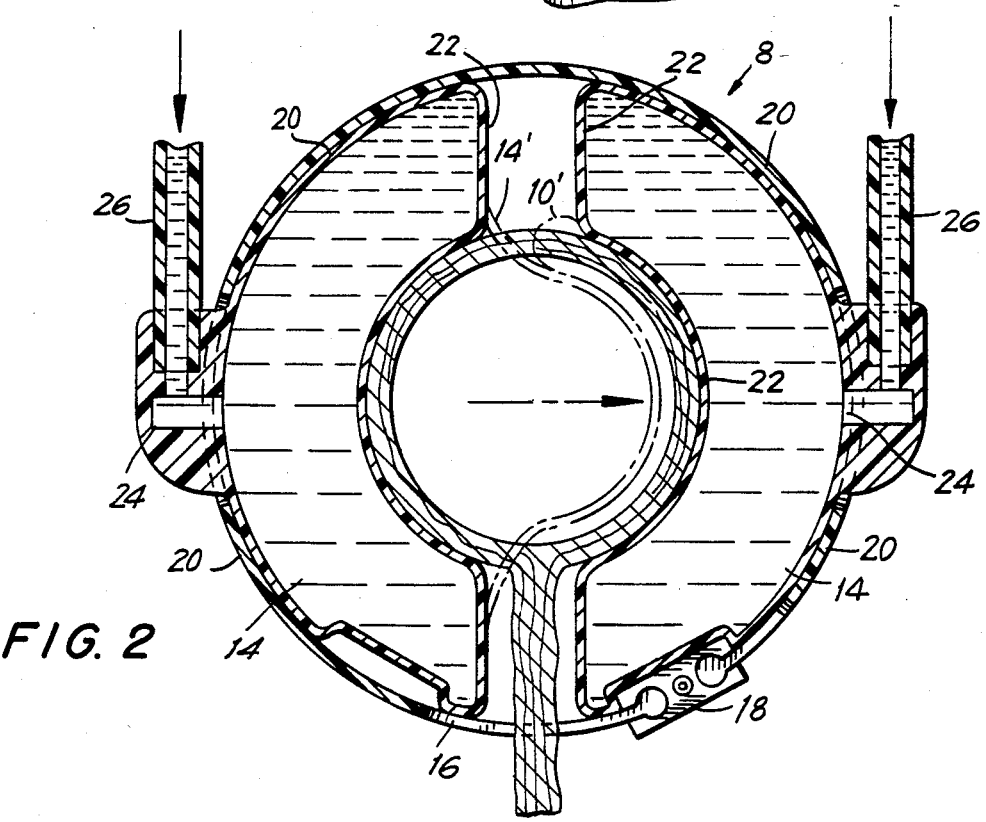
FIG. 2 is a cross-sectional view taken along line 2—2 of FIG. 1.

Referring know to the drawings and in particular to FIGS. 1 and 2 wherein an artificial sphincter, generally indicated by the numeral 8, is shown in operable position for occluding a body vessel 10, such as the colon or urinary tract. The artificial sphincter 8 includes a cuff 12 having two cuff chambers 14 attached to and interconnected by a reinforcing belt 16. The opposing ends of the belt 16 are fastened together by a mechanical latch 18 so as to retain the device in its operable position about the vessel 10.

The cuff chambers 14 are made of a flexible biocompatible air impermeable material. Each chamber 14 has a substantially hemicylindrical shape with an outer curved surface 20 and an inner surface 22, as shown in FIG. 2. Each chamber 14, includes an opening or port 24, along its outer surface 20, for receiving and discharging a fluid medium therethrough via tubing 26, during inflation and deflation, respectively. The tubing is interconnected to the appropriate reservoirs and pumps (not shown) which produce the inflation and deflation, as described, for example, in U.S. Pat. No. 4,167,952 to Reinicke, incorporated herein by reference. Inflated cuff chamber 14' and constricted body vessel 10' are indicated by dotted lines in FIG. 2.

The elongated reinforcing belt 16 extends along the outer curved surface 22 of cuff chambers 14, and is secured thereto. The belt is preferably made out of a silicone elastomer which is mesh reinforced.

Figure 3:
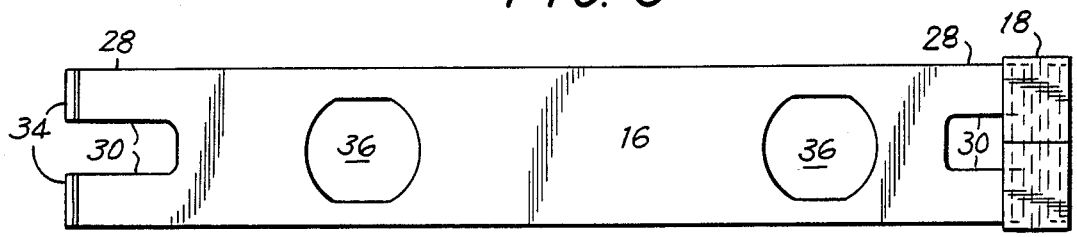
FIG. 3 is a plan view of a cuff belt which includes the latch of the current invention.

Referring now to FIG. 3, the belt 16 has two identical opposing end portions 28, each of which are bifurcated to form two flexible fingers 30, separated by a space. As can be seen most clearly in FIG. 1, the fingers 30 are designed to be capable of insertion through the mesentery 32 of the vessel 10 without interfering with the supply of blood to the tissue of the vessel wall 33. The fingers 30 are inserted through the mesentery 32 prior to fastening to the latch 18. At the terminal edge of each finger 30 is an enlarged bead 34, which is substantially cylindrical in shape. Each of the four beads 34 are secured to the latch 18 in the manner described below so as to secure the artificial sphincter 8 in its operable position about the vessel 10. The belt 16 also includes two windows 36 which allow the tubing 26 to extend from the ports 26 through the belt 16.

Figure 4:
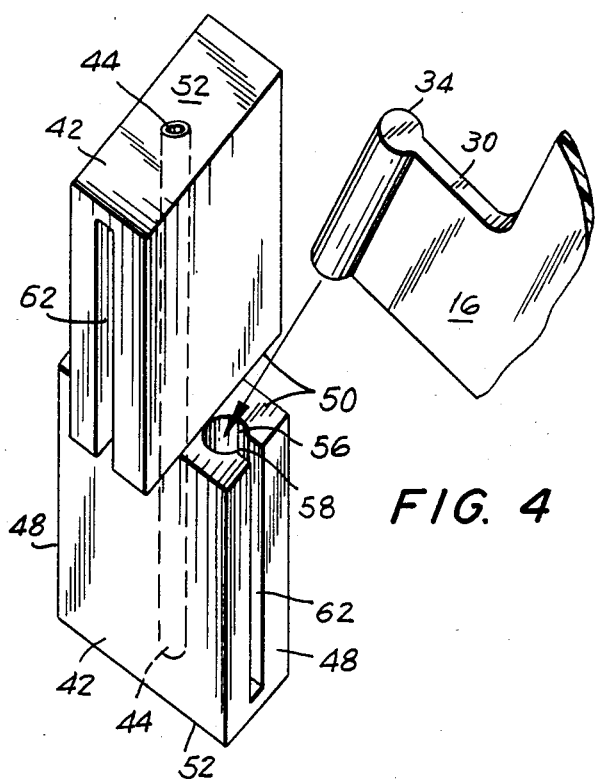
FIG. 4 is a perspective view of the latch shown in FIG. 3.
Figure 5:
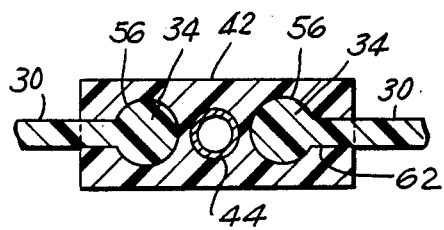
FIG. 5 is a cross-section view invention taken along line 5—5 of FIG. 1.

Referring now to FIGS. 4 and 5, the latch includes two identical substantially rectangular block-like components 42, which are mounted on a common axle or pin 44 so as to be independently rotatable about the pin and rotatable relative to one another. Each component 42 has two side surfaces 48, an inner surface 50 and outer surface 52. The inner surfaces 50 of the components 42 are adjacent and oppose or face each other across a slight gap. This gap or offset permits the components to rotate without interference. Near and parallel to the side surfaces 48 of each component 42 is a cylindrical cavity 56 for snugly receiving and retaining the cylindrical bead 34 from a finger 30 of a belt end 28.

Each of the four cavities 56 has an inlet or port 58 in the inner surface 50 of the corresponding component 42. The cavity 56 terminates within the respective component 42 so that the port 58 is the only entrance or exit for the bead 34 into the cavity 56. The components 42 have a slit 62 extending through the side surfaces 48 and along the length of each cavity 36 which permits the finger portion 30 of the belt 16 to project through the slit 62 when the bead 34 is inserted into the cavity 56. The cavities 56 are dimensioned so as to snugly accommodate the entire bead 34 while permitting the finger portions 30 to extend through the slits 62.

As shown most clearly in FIG. 4, insertion of the end portions 17 involves rotation of at least one of the components 42 so as to provide external accessibility to each port 58. A bead 34 is slid into each cavity through the exposed port 58, while the finger portion 30 is simultaneously slid into the slit 62. The flexibility of the finger portions facilitate the insertion of the bead. Suitable rotation of each component 42 permits the insertion of a bead 34, into each cavity 56, so that the ends of the belt are latched together. The length of the belt is predeterminedly selected so that when the ends are latched the belt is put into tension. The tension orients and maintains the latch 18 in a stabilized position (see FIG. 1). When the components are in this stabilized position, the ports 58 are externally inaccessible so that insertion or removal of the bead portion 34 and corresponding belt end 17 is prevented.

Unintentional removal of the fingers 30 from the latch 18 is especially difficult since it would require both rotation of a component 42 and the application of a force to a finger 30 which is directed towards port 58. Only a person intentionally removing this latch from the belt when it is in the stabilized position would be capable of applying the required combination of forces necessary to disconnect the latch from the belt.

The invention claimed is:

1. A latch for securing the ends of a belt together so as to encircle an inflatable cuff of an artificial sphincter, said latch comprising: two components mounted on a common pin, at least one of said components being at least partly rotatable about said pin relative to said other component, each of said components including at least one cavity for receipt of a portion of the belt end, said cavities being accessible for insertion or removal of said belt portion upon suitable rotation of at least one of said components, said inserted belt ends being captured within said cavities when said two components are in a rotatably stabilized condition.

2. The latch of claim 1 wherein said components are in a rotatably stabilized condition when said belt ends are inserted in said latch and said belt is in tension upon inflation of said inflatable cuff by an inflating means.

3. The latch of claim 1 wherein at least one of the belt ends is bifurcated into two fingers, each terminating in an enlarged bead, each cavity being predeterminedly dimensioned for snugly accommodating a bead therein, each component having a slit communicating with each of said cavities permitting the fingers to extend therethrough when said beads are inserted into said cavities.

4. The latch of claim 3 wherein each component has an opposing surface, said surfaces being offset to permit rotation of at least one of said components, each of said cavities having a port in an opposing surface, said offset being dimensioned so as to prevent insertion or removal of said beads through said ports and between said opposing surfaces when said components are in a rotatably stabilized position.

5. The latch of claim 4 wherein the belt is bifurcated at each end, each of said components having two cavities, and each component accommodating a bead from each opposing belt end.

6. The latch of claim 5 wherein said of two components are block-like in shape, each component having two side surfaces parallel to said pin and an inner and outer surface perpendicular to said pin, said inner surface of each component opposing each other.

7. The latch of claim 6 wherein said cavities are parallel to said pin, each cavity having a port in said inner surface of said corresponding component, each of said slits extending through a side surface of each component and interconnecting with said cavity.

8. The latch of claim 7 wherein said components are identical.

* * * * *